United States Patent
Lais et al.

(10) Patent No.: US 11,354,528 B2
(45) Date of Patent: Jun. 7, 2022

(54) READING A PLURALITY OF CODES

(71) Applicant: SICK AG, Waldkirch (DE)

(72) Inventors: Stefan Lais, Waldkirch (DE); Carl Hafner, Waldkirch (DE); Rainer Maier, Waldkirch (DE); Karsten Heuser, Waldkirch (DE); Matthias Held, Waldkirch (DE); Helge Schlegel, Waldkirch (DE)

(73) Assignee: SICK AG, Waldkirch (DE)

( * ) Notice: Subject to any disclaimer, the term of this patent is extended or adjusted under 35 U.S.C. 154(b) by 0 days.

(21) Appl. No.: 17/116,788

(22) Filed: Dec. 9, 2020

(65) Prior Publication Data
US 2021/0182520 A1    Jun. 17, 2021

(30) Foreign Application Priority Data
Dec. 12, 2019    (DE) .................... 10 2019 134 064.0

(51) Int. Cl.
*G06K 7/14*    (2006.01)
*G06T 7/13*    (2017.01)
(Continued)

(52) U.S. Cl.
CPC .............. *G06K 7/1447* (2013.01); *A61J 1/00* (2013.01); *G06K 7/10584* (2013.01);
(Continued)

(58) Field of Classification Search
CPC ............ G06K 7/1447; G06K 7/10584; G06K 7/1443; G06K 7/1465; G06K 7/1491;
(Continued)

(56) References Cited

U.S. PATENT DOCUMENTS

| 7,090,137 B1 | 8/2006 | Bennett |
| 2006/0081712 A1* | 4/2006 | Rudeen ............... G06K 7/14 |
| | | 235/462.08 |

(Continued)

FOREIGN PATENT DOCUMENTS

| DE | 202019104044 U1 | 10/2019 |
| EP | 2874924 | 1/2014 |

(Continued)

OTHER PUBLICATIONS

Safe-Ident Code Offline, STRELEN Control Systems GmbH, Nov. 20, 2020, https://info.strellen.net/services/en/cde02/.

*Primary Examiner* — Matthew Mikels
(74) *Attorney, Agent, or Firm* — Nath, Goldberg & Meyer; Jerald L. Meyer

(57) ABSTRACT

A code reading device for the parallel reading of a plurality of codes on a plurality of objects arranged next to one another is provided that has a camera unit having at least one camera head for recording an image of the objects, a control and evaluation unit that is configured to localize code zones of the codes in the image and to read the code information of the codes, and a display unit to present the image and to mark the read codes and/or objects having read codes, Here a hand reading unit for reading codes is provided to subsequently read codes not read by means of the camera unit and to transfer the subsequently read code information to the control and evaluation unit.

19 Claims, 2 Drawing Sheets

(51) Int. Cl.
*A61J 1/00* (2006.01)
*G06K 7/10* (2006.01)
*G16H 70/40* (2018.01)
*G06F 3/041* (2006.01)
*G06Q 30/00* (2012.01)
*G06Q 50/26* (2012.01)

(52) U.S. Cl.
CPC ......... *G06K 7/1443* (2013.01); *G06K 7/1465* (2013.01); *G06K 7/1491* (2013.01); *G06T 7/13* (2017.01); *A61J 2205/40* (2013.01); *G06F 3/041* (2013.01); *G06K 7/1097* (2013.01); *G06K 7/10861* (2013.01); *G06K 2007/10524* (2013.01); *G06Q 30/0185* (2013.01); *G06Q 50/26* (2013.01); *G06T 2207/30242* (2013.01); *G16H 70/40* (2018.01)

(58) Field of Classification Search
CPC ............. G06K 7/10861; G06K 7/1097; G06K 2007/10524; G06K 7/10722; A61J 1/00; A61J 2205/40; G06T 7/13; G06T 2207/30242; G06F 3/041; G06Q 30/0185; G06Q 50/26; G16H 70/40

See application file for complete search history.

(56) References Cited

U.S. PATENT DOCUMENTS

2013/0020391 A1\* 1/2013 Olmstead ........... G06K 7/10762
 235/438
2016/0188939 A1 6/2016 Sailors et al.

FOREIGN PATENT DOCUMENTS

| EP | 3040906 | A1 | 7/2016 |
| WO | 2014015058 | A1 | 1/2014 |
| WO | 2019149908 | A1 | 8/2019 |

\* cited by examiner

READING A PLURALITY OF CODES

FIELD

The invention relates to a code reading device and to a method for the parallel reading of a plurality of codes on a plurality of objects arranged next to one another.

BACKGROUND

In accordance with the EU falsified medicinal products directive 2011/62/EU and the delegated regulation (EU) 2016/161, all individual pharmaceutical packs subject to prescription must be monitored from production up to the end customer and must be compared with a EU database to identify possible falsifications. Similar demands can also be found in the tobacco products directive 2014/40/EU.

The individual packs therefore have to be provided with an individual code that includes a unique serial number. These codes have to be read on every transfer to verify the correct origin with the aid of the database and thus to maintain the verification chain.

DE 20 2019 104 044 U1 describes a system of verifying and logging out medication packaging with reference to individual serial numbers specific to the packaging. It is here a question of how the communication of the code information can take place, for example, between a hospital pharmacy and a third party provider of a verification database. The actual detection of the codes, that is the code reading, is not looked at in any more detail.

WO 2019/149908 A1 describes a method of monitoring the supply chain of a product. Different cryptographic methods, including a blockchain, are proposed for this purpose. This approach does not utilize said EU database.

To be able to verify all products on a transfer, a scan solution for the codes is required that guarantees a reading rate of 100%. This relates, for example, to wholesalers of pharmaceutical products subject to prescription for which said EU regulations must absolutely be observed. This problem, however, occurs in general form with all serialized scanning procedures both with optical codes and, for example, with RFID.

The specific challenge comprises completely reading a plurality of codes of, for example, a box full of medicinal product packs. One possibility is to read the individual packs or their codes one after the other using a hand scanner. This is very laborious and exhausting work. If now in addition not all of the codes have not been read at the end of the scanning procedure, the operator does not receive any location information on any pack the scanning procedure was not successful on. There is therefore no alternative to repeating the entire scanning procedure until the number or read codes corresponds to the number of packs.

Another approach comprises using a camera based code reader that records an image of the code and thus no longer reads it serially, but rather in parallel. This substantially simplifies the scanning procedure and additionally opens up the possibility of presenting which codes have already been read on a display. The system, however, then does not offer any satisfactory solution on how to deal with the unread codes. Only the possibility is offered to repeat the parallel process for so long until there are no longer any unread codes. A large number of reading errors will, however, not be able to be reproduced so that this often does not meet its aim. The alternative remains of removing packs with unread codes until the remaining codes have been completely read. An individual solution then has to be found for the remaining packs. Such a system is, for example, offered by the Strelen corporation on its internet site under the heading offline code verification.

Code reading systems are known that provide feedback with respect to unread codes. A hand scanner in accordance with U.S. Pat. No. 7,090,137 B1, for example, projects different information related to the reading procedure or the reading result onto the code or into the proximity of the code. The above-described sequential manual reading could thus be simplified where required in that reading errors become immediately recognizable; however, the exhaustive work of detecting all the packs by hand is not thereby dispensed with.

A reading tunnel is known from WO 2014/015058 A1 through which packages are conveyed one after the other. Whether a code has been read on the package or not is displayed by light in different colors, for example red and green, after the reading zone. The display takes place with the aid of LEDs at the side or by a projection onto the package. Such a reading tunnel that processes packages after one another is slow and laborious for the verification of a larger number of packs in comparison with a compact parallel reading.

SUMMARY

It is therefore the object of the invention to improve the parallel reading of a plurality of codes.

This object is satisfied by a code reading device and by a method for the parallel reading of a plurality of codes on a plurality of objects arranged next to one another in accordance with the respective independent claim. The code reading device is configured for a parallel mass reading of also larger groups of objects having codes. A camera unit having at least one camera head is provided for this purpose that records an image of the objects with the codes. A control and evaluation unit identifies the code zones in the image and reads the codes. A display unit shows the image and marks the read codes or objects, either directly, for example by a color highlighting, borders, or the like, or indirectly, for example via the indication of coordinates. The number of read codes is preferably additionally displayed.

The invention starts from the basic idea of adding a hand reading unit for reading codes, for example a hand scanner, that belongs to the system to the code reading device. The hand reading device is part of the code reading device in that it is physically connected thereto or in that there is at least a wireless communication connection to its control and evaluation unit. Those codes are subsequently read by means of the hand reading unit that could not be read from the image of the camera unit. The corresponding subsequently read code information is transmitted to the control and evaluation unit that can thus collect the read codes of both the camera unit and the hand reading unit, can compare them with each other, and can count them.

The invention has the advantage that a reading rate of 100% can be achieved in a particularly simple and comfortable manner by the manual subsequent reading. Since the hand reading unit is integrated in the code device, it is always immediately available and no special steps are required to combine its reading results with the reading results of the parallel reading process. Dealing with unread codes within the system is not possible at or or at most only very laboriously, as described in the introduction, in the prior art. Either the total reading procedure is repeated there, which is time-consuming and which in many cases only produces the same error as before, or the objects having unread codes have to be separated and treated by a separate solution.

The code reading device preferably has a plurality of camera heads, with the control and evaluation unit preferably being configured to assemble (i.e. stitch) the image data of the camera heads into one common image and/or to read the codes in the respective image data and to compare them with one another. The plurality of camera heads serve to record a larger image and/or an image of higher resolution. The individual images of the camera heads can be merged to one image than is then treated as the image of only one single camera head or respective codes are read in the individual images, with the evaluation of the image also being able to be parallelized. In other words, the detection results can be combined on the level of image data or at the latest on the level of code content. The overlap of the fields of view of the camera heads is preferably larger than a code for then every code in an image zone of the same camera can be read and no transition regions have to be considered (stitching). Doubling due to reading from the images of a plurality of camera heads is recognized due to the unique serial number of the codes.

The objects are preferably located in a conveying unit, for example in a box, on a pallet, or the like. The camera unit detects this conveying unit from the relevant side where the codes can be recognized, in particular from a plan view. The box is packed for this purpose, for example, such that the top sides of the objects bearing a code face upward.

The objects are preferably packs each having a unique code, in particular packs for medicinal products or cigarettes. The pharmaceutical and cigarette industries are branches in which serialized codes play a decisive role due to EU law. The codes, for example, include the serial number and other required information for the verification in the central EU database.

The control and evaluation unit is preferably configured to recognize the respective objects as a rectangle of detected edges and in particular to count them. In a large number of real applications, for instance also for packs for medicines or cigarette packs, the geometry of the objects is very simple and this can be used to implement a simple segmentation in the image evaluation. Parallelepiped-shaped packs are rectangles disposed next to one another in the image from the perspective of the camera unit. An edge detection in the image and a combination to form rectangles can thus separate and localize the objects. This has a plurality of advantages. On the one hand, the control and evaluation unit can in this manner determine the total number of detected objects itself that can then be compared with the number of read codes to determine whether all the codes have been read or how many codes have to be subsequently read using the hand reading device. On the other hand, all the objects can then be marked whose codes have already been read or have not yet been read and this in turn simplifies the recognition of the codes still to be subsequently read using the hand reading unit. In principle, a complex segmentation is alternatively also conceivable without prior knowledge of the geometry of the objects; however, it is then substantially more difficult to really separate all the objects with the required reliability. A segmentation error would falsely result in an assumption of a reading rate of 100%.

The control and evaluation unit is preferably configured to check whether a subsequently read code had already been previously read. If the hand reading unit transmits the code content of a further read code, this by no means automatically means that the total number of read codes is increased. The operator could have detected a code already read via the camera unit or a previously already subsequently read code. This is checked and recognized via the unique code information so that code information transmitted by the hand reading unit relating to already known codes can be ignored and only new code information is added or the number of read codes is accordingly incremented. A corresponding test for already known codes in another respect preferably also takes place for the parallel reading via the camera unit, to intercept either multiple records of a plurality of camera heads, repeat recordings, or a plurality of codes applied redundantly to an object.

The control and evaluation unit is preferably configured to mark codes and/or objects with respect to which no code has yet been read. If the objects are tightly packed as with pharmaceutical packs or cigarette packs in a transport container, the unread codes are therefore very easily recognizable because the marking for a read code is missing there. It can nevertheless be helpful to explicitly add a marking of the unread codes. Different colors are, for example, used, for instance the read codes or associated codes are marked in green and the unread codes or associated objects in red.

The control and evaluation unit is preferably configured to localize subsequently read codes. The hand reading unit reads the code where the operator directs it, Without any further measures, the control and evaluation unit then only experiences the code information, but not the object or the location in the image to which this code information belongs. In accordance with this advantageous embodiment, the subsequently read code is additionally associated with a specific object or location in the image. This can take place by a manual input, a separate localization by a sensor system, or the like of the hand reading unit or by additional image evaluation.

The control and evaluation unit is preferably configured to localize a reading light spot produced on the objects by the hand reading unit. This is a particularly simple implementation option of localizing subsequently read codes. If the control and evaluation unit recognizes a reading light spot in the image in a close time connection and receives the code information relating to a read code from the hand reading unit, this code information is linked to the code or object having the reading light spot.

The control and evaluation unit is preferably configured to mark a subsequently read code. The operator thus obtains feedback that this code has now been subsequently read. The marking in the image at the subsequently read code or associated object changes, for example, for instance from red to green, or the subsequently read code is temporarily highlighted by a separate distinguishable marking, for instance by a further color, a particularly bright or thick marking or the like.

The display unit is preferably configured as a touchscreen via which the code reading device is controlled. The display unit can thereby simultaneously satisfy the function of a control unit (HMI, human machine interface), with additional control elements remaining possible. The touchscreen can also be used for an alternative localization of subsequently read codes. The operator touches an area of the display to link a just subsequently read code or immediately to be subsequently read code with this location.

The camera unit preferably has a changeable lighting unit, in particular having a plurality of illumination modules, with the control and evaluation unit being configured to record the objects multiple times under different lighting for the parallel reading of the codes, in particular under lighting from different directions. The lighting unit is able to generate different illumination scenarios under which, where possible, different or more codes can be read. The intensity of illumination and/or the direction of the lighting is/are in particular varied for this purpose. A preferred embodiment provides positioning a respective one illumination module to the right and left of the camera and to produce three shots when illuminating from a respective one side or from both sides. Disadvantageous effects due to inherent glare and underdrive and overdrive are thus compensated. The plurality of images are first merged, depending on the embodiment, to an image of better quality, similar to an HDR (high dynamic range) shot, or the control and evaluation unit reads codes one after the other from a plurality of images or from each image, with doubling being able to be sorted out using the serial number.

The control and evaluation unit is preferably configured for an aggregation mode in which an aggregation code is initially read and the codes read afterward are associated with this aggregation code. The aggregation code is preferably provided via the database or its operator via which the verification takes place. A plurality of verified codes can be combined under the aggregation code. Such an aggregation code is, for example, applied to a box, pallet, or other conveying unit that is then preferably closed or sealed. As long as the objects having the codes collected under the aggregation code remain together, it is sufficient only to read and to verify the respective aggregation code under which all the associated codes are found as belonging together in the database.

The code reading device preferably has an interface to a higher ranking system in which the read codes are verified and/or logged out. The higher ranking system is preferably a network or a cloud having a central database. This database is frequently operated by a third party provider that verifies and logs out the codes transferred there as required. Verify here means that the authenticity of the code is confirmed to preclude falsifications, while on the logging out the transfer to the end customer has taken place where the object, for example a medicinal product, is consumed and is at least not further monitored. Reference is again made to DE 20 2019 104 044 U1 named in the introduction for further details.

The method in accordance with the invention can be further developed in a similar manner and shows similar advantages in so doing. Such advantageous features are described in an exemplary, but not exclusive manner in the subordinate claims dependent on the independent claims.

BRIEF DESCRIPTION OF THE DRAWINGS

The invention will be explained in more detail in the following also with respect to further features and advantages by way of example with reference to embodiments and to the enclosed drawing. The Figures of the drawing show in.

DETAILED DESCRIPTION

Figure 1:
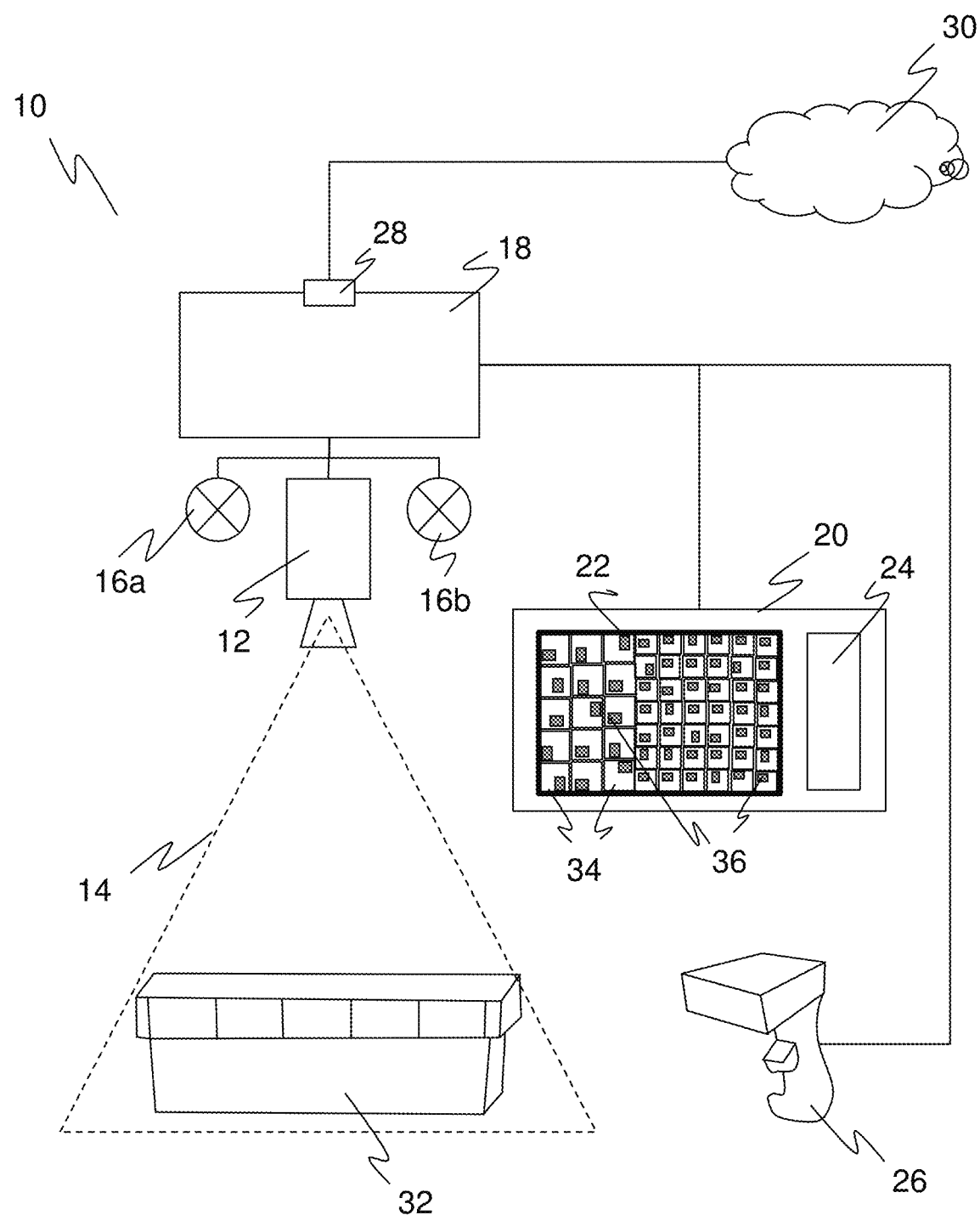
FIG. 1 an overview representation of a code reading device with a camera unit for a parallel reading of codes and a hand reading unit for subsequently reading a code.

FIG. 1 shows an overview representation of a code reading device 10. It is configured as a complete system that provides a camera based parallel reading process to read a plurality of codes and additionally provides the option of subsequently reading any codes not read by the parallel reading process within the complete system and thus achieving a reading rate of 100%.

The code reading device 10 has a camera unit 12 whose camera head is only shown symbolically in FIG. 1. The camera unit 12 comprises, without any separate illustration, a preferably high resolution image sensor, a suitable optics, and an interface to at least the output of the respective recorded image data. If the field of view 14 of a single camera head is not sufficient, a plurality of camera heads can be arranged next to one another. A lighting unit that is equipped with two illumination modules 16a-b. at both sides in FIG. 1 is associated with the camera unit 12. The illumination modules 16a-b are preferably particularly fast with correspondingly powerful LEDs or laser diodes.

A control and evaluation unit 18 makes use of the image data of the camera unit 12, evaluates them, and controls the illumination modules 16a-b during the recordings. Images of the camera unit 12 and evaluation results can be presented on a display 20. The display 20 is preferably configured as a touchscreen and then simultaneously serves as an operating unit of the code reading device 10. A first zone 22 for presenting images and a second zone 24 for control elements are, for example, provided on the display 20.

A hand scanner 26 is furthermore connected to the control and evaluation unit 18 in a wireless or wired manner. The control and evaluation unit 18 communicates with a higher ranking system, in particular with a cloud 30, via an interface 28 and is thereby in contact with a database in the cloud 30. The interface 28 can be configured according to every known standard, for example wired or wireless, for example by WiFi or cellular radio. A box 32 is arranged in the field of view 14 of the camera unit 12 and a plurality of objects 34 having optical codes 36 applied thereto are located therein. The codes 36 are serialized; they can consequently be uniquely identified. Additional information with respect to a package content, a batch number, a date of manufacture or a date of expiry, a delivery address, and the like is also possible.

The different elements of the code reading device 10 are preferably mechanically connected to one another by a frame so that the complete system also physically forms a unit. The camera unit 12 together with the illumination modules 16a-b is fastened to the frame such that the box 32 is recorded within the depth of field zone when it is placed on a surface provided at the frame. The control and evaluation unit 18 can be hidden in the frame and it is accessed via the display 20 designed as a touchscreen and/or via alternative control elements that are each attached to the frame in an easily accessible manner. At least one placement station for the hand scanner 26 that also charges a wireless device is preferably provided at the frame or the hand scanner 26 can be connected by a connection line or by a holder cord that prevents the hand scanner 26 from being removed from the code reading device 10.

To now read all the codes 36 in the box 32, an image of the box with the objects 34 located therein and the codes 36 is recorded by the camera unit 12 as is shown by way of example in the first zone 22 of the display 20. The perspective of the camera unit 12, here in the plan view, and the orientation of the objects 34 in the box 32 are coordinated with one another so that all the codes 36 are visible in the image.

The control and evaluation unit 18 localizes the code zones with the codes 36 by means of code image processes and reads their code content. All one-dimensional and two-dimensional code standards are conceivable here. The camera based reading of optical codes is known per se and will not be described in any more detail here.

In the case of a plurality of camera heads, every camera head records its part section of the field of view 14. These image data are then merged and the codes 36 are read in the common image. Alternatively, codes 36 are read from the individual images and the data are then only collected at the level of read code information.

A plurality of recordings are produced in preferred embodiments. It is again alternatively conceivable to subsequently first merge the image data to obtain a higher quality image and to read the codes 36 therein or already to read codes 36 in the respective images to thus ultimately carry out a plurality of attempts on different image data. An example for the detection of higher quality image data by multiple recording is HDR (high dynamic range).

Such multiple recordings are preferably produced in different illumination scenarios in that different illumination modules 16a-b are activated and/or their illumination intensity is varied. An example is a three-stage illumination sequence with three shots for which first the left illumination module 16a, then the right illumination module 16b, and finally both illumination modules 16a-b are switched on. Reading errors due to interfering reflections are thereby minimized. The number of illumination modules 16a-b and thus the number of possible illumination scenarios and the order in the illumination sequence is not fixed. The illumination scenarios and multiple recordings are rather parameterized with respect to the application.

All the codes 36 are only read in the ideal case due to the parallel reading process based on the image data of the camera unit 12. To achieve a complete reading rate of 100%, following this the previously unreadable codes 36 are subsequently read by the hand scanner 26. The operator is here assisted by the display 20 on which, for example, the already read codes 36 or the locations of zones recognized as an object 34 or code 36 are marked in which subsequently reading has to take place. In addition, the number of read codes 36 and, provided this number is predefined or has been determined by image evaluation, also the number of codes 36 present in total is displayed. These possibilities will be explained in more detail below with reference to FIGS. 2 and 3.

The code information in a central database, that is here implemented in the cloud 30 by way of example, is verified via the interface 28 and is also logged out on transfer to the end customer. The database, in particular a pharmaceutical or tobacco product verification platform, is operated by a provider as a rule. The control and evaluation unit 18 provides all the steps of communication required on the side of the code reading device 10. The database and the specific embodiment of the communication with the database are not the subject of the invention and reference is again made for this purpose, for example, to DE 20 2019 104 044 U1 and to the possibilities of safeguarding by cryptography and blockchain in accordance with WO 2019/149008 A1.

Figure 2:
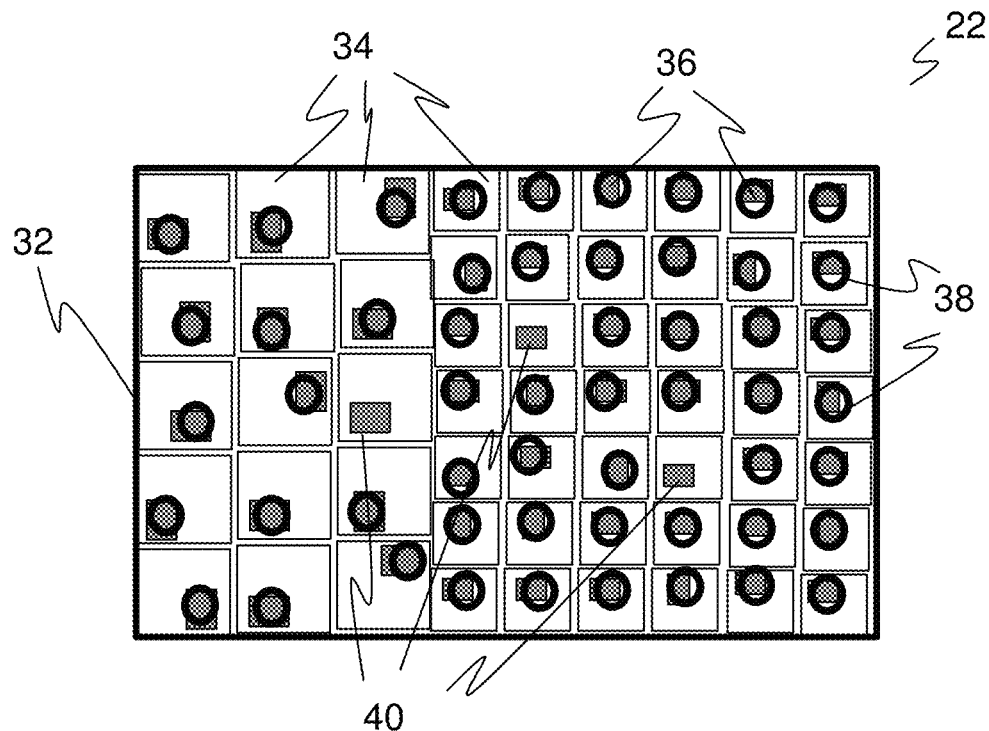
FIG. 2 an exemplary camera image of a plurality of objects having codes and marking of the codes read by means of the camera unit.
Figure 3:
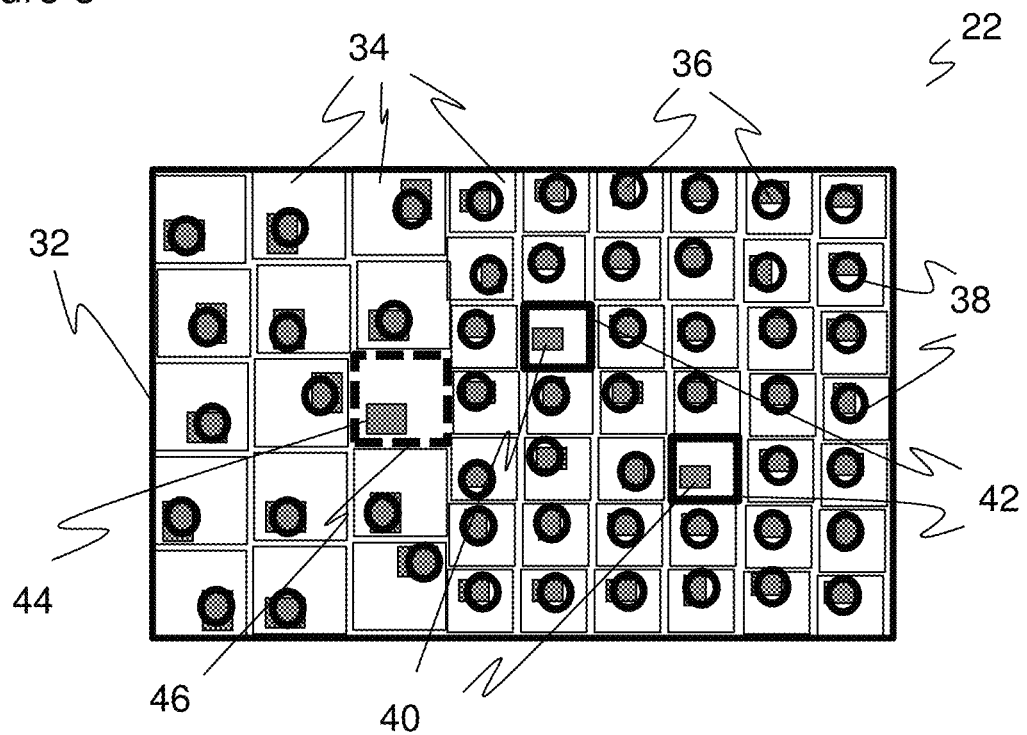
FIG. 3 the camera image in accordance with FIG. 2 now additionally with a separate marking of the codes not readable by means of the camera unit.

FIG. 2 shows in an enlarged representation an exemplary image of the box 32 such as can be presented to the operator in the first zone 22 of the display 20. The codes 36 read in the parallel reading process on the basis of the recording of the camera unit 12 are marked by a first marking 38, here purely by way of example by a circle, in particular in a green color. The operator can in this way immediately recognize still unread codes 40 and can subsequently scan them with the hand scanner.

The image evaluation is restricted in this embodiment to identify code zones and to read as many codes 36 as possible. The location information of the codes 36 read in the parallel process is therefore known to thus position the first markings 38 at the correct positions. The objects 34 themselves were not segmented, however. The unread codes 40 were, however, possibly by all means recognized as codes 36, for example, with reference to their contrast; the decoder had only subsequently failed to read the code information. It is therefore conceivable in a further embodiment to provide unread codes 40 with a second marking, for example in red, to highlight even more clearly where the hand scanner 26 still had to be directed.

FIG. 3 again shows an exemplary image of the box 32 to explain some further embodiments with a display of additional information to assist the operator in the subsequent reading. The objects 34 are segmented by image evaluation in a variant. This has two advantages. On the one hand, the associated objects 34 can be marked as a second marking 42 for unread codes 40, for example by a border to improve the visibility. This second marking 42 is also possible when, on the parallel reading attempt of a code 36, it has not even been recognized that it is a code 36 at all. For now the associated object 34 that necessarily has to bear an unread code if no code was read on it is identified by the segmentation. On the other hand, the objects 34 can now be counted in the box 32, i.e. the total number of read codes 36 to be achieved is known without prior knowledge or manual counting. The control and evaluation unit 18 thus known when all the codes 36 have to be read and it is no longer necessary to subsequently read anything.

Since the objects 34 are as a rule parallelepiped-shaped packs of possibly also at least roughly known dimensions, a powerful universal object segmentation is by no means required but would also be able to be used per se. A comparatively simple edge detection with a subsequent combination of rectangles is rather sufficient. This reduces the complexity of the object segmentation and reduces the error rate since the objects should in particular be very reliably segmented and counted for an automatic determination of the total number as an evaluation measure for a reading rate of 100%.

If the operator subsequently reads a specific previously unread code 44, the control and evaluation unit 18 can recognize whether this code 44 had already been read once with reference to the unique serial code. However, it initially has no possibility of localizing the subsequently read code 44 within the image since the hand scanner 26 only delivers the code content. It is, however, a substantial relief for the operator if the subsequently read code 44 is marked as read in future or Is given a special marking 46 and this then preferably changes to a first marking 38 as read.

There are several possibilities how this localization can nevertheless be achieved. In principle, the hand scanner 26 could also deliver this information by separate localization and distance measurement. The operator could also establish the relationship himself in that the zone of the just subsequently read code 44 or of the code 44 subsequently read in the following is, for example, touched on the touchscreen of the display 20. The subsequently read code 44 is particularly preferably automatically recognized by image evaluation. The reading light spot that the hand scanner 26 generates on the subsequently read code 44 is localized for this purpose. With a correspondingly tight time relationship between the localization of the reading light spot and the transmission of a code content from the hand scanner 26, the control and evaluation unit 18 links these two events and so recognizes the location of the subsequently read code 44 in the image.

In a preferred further development, whole groups of codes 36 are not always verified, but rather a plurality of codes 36 are combined under a so-called aggregation code and are compared with the database via this aggregation code. An aggregation code is, for example, stuck onto a closed box 32 after all the codes 36 therein have been read and verified. The total content of the box 32 can now be detected with considerably reduced effort via the aggregation code. The aggregation code is provided by the database operator in the cloud 30 where the link between the aggregation code to the codes 36 combined thereunder also later takes place.

The code device 10 can provide an aggregation mode for this purpose. In this respect, the aggregation code is read first, either by means of the camera unit 12 or by means of the hand scanner 26. Codes 36 are subsequently read using the above described method and logged onto the aggregation code.

The invention claimed is:

1. A code reading device for the parallel reading of a plurality of codes on a plurality of objects arranged next to one another, the code reading device comprising:
   a camera unit having at least one camera head for recording an image of the objects, a control and evaluation unit that is configured to localize code zones of the codes in the image and to read the code information of the codes, a display unit to present the image and to mark the read codes and/or objects having read codes, and a hand reading unit for reading codes to subsequently read codes not read by means of the camera unit and to transfer the subsequently read code information to the control and evaluation unit,
   wherein the control and evaluation unit is configured to check whether a subsequently read code had already been previously read.

2. The code reading device in accordance with claim 1, that has a plurality of camera heads, with the control and evaluation unit being configured to assemble the image data of the camera heads into one common image and/or to read the codes in the respective image data and to compare them with one another.

3. The code reading device in accordance with claim 1, wherein the objects are located in a conveying unit.

4. The code reading device in accordance with claim 1, wherein the objects are packs each having a unique code.

5. The code reading device in accordance with claim 4, wherein the packs are for one of medicinal products and cigarettes.

6. The code reading device in accordance with claim 1, wherein the control and evaluation unit is configured to recognize the respective objects as a rectangle of detected edges.

7. The code reading device in accordance with claim 6, wherein the control and evaluation unit is further configured to count the respective objects.

8. The code reading device in accordance with claim 1, wherein the control and evaluation unit is configured to mark at least one of codes and objects with respect to which no code has yet been read.

9. The code reading device in accordance with claim 1, wherein the control and evaluation unit is configured to localize subsequently read codes.

10. The code reading device in accordance with claim 1, wherein the control and evaluation unit is configured to localize a reading light spot produced on the objects by the hand reading unit.

11. The code reading device in accordance with claim 1, wherein the control and evaluation unit is configured to mark a subsequently read code.

12. The code reading device in accordance with claim 1, wherein the display unit is configured as a touchscreen via which the code reading device is controlled.

13. The code reading device in accordance with claim 1, wherein the camera unit has a changeable lighting unit, and wherein the control and evaluation unit is configured to record the objects multiple times under different lighting for the parallel reading of the codes.

14. The code reading device in accordance with claim 13, wherein the changeable lighting unit has a plurality of illumination modules.

15. The code reading device in accordance with claim 13, wherein the control and evaluation unit is configured to record the objects multiple times under lighting from different directions.

16. The code reading device in accordance with claim 1, wherein the control and evaluation unit is configured for an aggregation mode in which an aggregation code is initially read and the codes read afterward are associated with this aggregation code.

17. The code reading device in accordance with claim 1, that has an interface to a higher ranking system in which the read codes are verified and/or logged out.

18. A method for the parallel reading of a plurality of codes on a plurality of objects arranged next to one another, in which method an image of the objects is recorded by a camera unit in which image code zones of the codes are localized and the code information of the codes is read,
   wherein the image is presented and the read codes and/or objects having read codes are marked,
   wherein a determination is made whether a subsequently read code had already been previously read
   and wherein codes not read by means of the camera unit are subsequently read by a hand reading unit for reading codes and the code information read by the camera unit and by the hand reading unit is collected together.

19. A code reading device for the parallel reading of a plurality of codes on a plurality of objects arranged next to one another, the code reading device comprising:
   a camera unit having at least one camera head for recording an image of the objects, a control and evaluation unit that is configured to localize code zones of the codes in the image and to read the code information of the codes, a display unit to present the image and to mark the read codes and/or objects having read codes, and a hand reading unit for reading codes to subsequently read codes not read by means of the camera unit and to transfer the subsequently read code information to the control and evaluation unit; and
   an interface to a higher ranking system in which the read codes are verified and/or logged out.

* * * * *